(12) United States Patent
Elibol et al.

(10) Patent No.: US 8,444,835 B2
(45) Date of Patent: May 21, 2013

(54) ELECTRONIC AND FLUIDIC INTERFACE

(75) Inventors: Oguz H. Elibol, Sunnyvale, CA (US); Jonathan S. Daniels, Palo Alto, CA (US); Stephane L. Smith, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 243 days.

(21) Appl. No.: 12/878,135

(22) Filed: Sep. 9, 2010

(65) Prior Publication Data

US 2012/0061239 A1 Mar. 15, 2012

(51) Int. Cl.
*G01N 27/403* (2006.01)

(52) U.S. Cl.
USPC .......................................... 204/411; 204/409

(58) Field of Classification Search
USPC .................................. 204/409–412
See application file for complete search history.

(56) References Cited

U.S. PATENT DOCUMENTS

| | | | |
|---|---|---|---|
| 5,145,565 A | 9/1992 | Kater et al. | |
| 5,393,399 A * | 2/1995 | Van den Berg et al. | 204/412 |
| 5,399,256 A * | 3/1995 | Bohs et al. | 204/409 |
| 5,795,714 A | 8/1998 | Cantor et al. | |
| 5,849,487 A | 12/1998 | Hase et al. | |
| 6,232,075 B1 | 5/2001 | Williams | |
| 6,952,651 B2 | 10/2005 | Su | |
| 6,972,173 B2 | 12/2005 | Su et al. | |
| 7,005,264 B2 | 2/2006 | Su et al. | |
| 7,238,477 B2 | 7/2007 | Su et al. | |
| 7,476,501 B2 | 1/2009 | Chan et al. | |
| 7,488,578 B2 | 2/2009 | Gumbrecht et al. | |
| 2002/0042388 A1 | 4/2002 | Cooper et al. | |
| 2002/0187515 A1 | 12/2002 | Chee et al. | |
| 2003/0116723 A1 | 6/2003 | Yoshida | |
| 2003/0155942 A1 | 8/2003 | Thewes | |
| 2003/0215816 A1 | 11/2003 | Sundararajan et al. | |
| 2003/0215862 A1 | 11/2003 | Parce et al. | |
| 2004/0005572 A1 | 1/2004 | Rosner et al. | |
| 2004/0067530 A1 | 4/2004 | Gruner | |
| 2004/0110208 A1 | 6/2004 | Chan et al. | |
| 2005/0019784 A1 | 1/2005 | Su et al. | |
| 2005/0026163 A1 | 2/2005 | Sundararajan et al. | |
| 2005/0106587 A1 | 5/2005 | Klapproth et al. | |

(Continued)

FOREIGN PATENT DOCUMENTS

CN 101118226 A * 2/2008
CN 201072428 Y * 6/2008

(Continued)

OTHER PUBLICATIONS

Derwent English language absract of Li et al. CN 201072428 Y, patent published Jun. 11, 2008.*

(Continued)

*Primary Examiner* — Alex Noguerola

(57) ABSTRACT

An electronic fluidic interface for use with an electronic sensing chip is provided. The electronic fluidic interface provides fluidic reagents to the surface of a sensor chip. The electronic sensing chip typically houses an array of electronic sensors capable of collecting data in a parallel manner. The electronic fluidic interface is used, for example, as part of a system that drives the chip and collects, stores, analyzes, and displays data from the chip and as part of a system for testing chips after manufacture. The electronic fluidic interface is useful, for example, nucleic sequencing applications.

25 Claims, 9 Drawing Sheets

U.S. PATENT DOCUMENTS

| | | |
|---|---|---|
| 2005/0186576 A1 | 8/2005 | Chan et al. |
| 2005/0214759 A1 | 9/2005 | Wlassof et al. |
| 2006/0029969 A1 | 2/2006 | Su et al. |
| 2006/0068440 A1 | 3/2006 | Chan et al. |
| 2006/0141485 A1 | 6/2006 | Su et al. |
| 2006/0199193 A1 | 9/2006 | Koo et al. |
| 2007/0059733 A1 | 3/2007 | Sundararajan et al. |
| 2007/0231790 A1 | 10/2007 | Su |
| 2007/0231795 A1 | 10/2007 | Su |
| 2008/0032297 A1 | 2/2008 | Su et al. |
| 2008/0160630 A1 | 7/2008 | Liu et al. |
| 2009/0170716 A1 | 7/2009 | Su et al. |
| 2010/0167938 A1 | 7/2010 | Su et al. |
| 2010/0267013 A1 | 10/2010 | Su et al. |

FOREIGN PATENT DOCUMENTS

| | | |
|---|---|---|
| WO | 03/054225 A2 | 7/2003 |
| WO | 03/058225 A1 | 7/2003 |
| WO | 2012/033666 A2 | 3/2012 |
| WO | 2012/033666 A3 | 6/2012 |

OTHER PUBLICATIONS

Derwent English language absract of Li et al. CN 101118226 A, patent published Feb. 6, 2008.*

English langauge translation of CN 201072428 Ye et al., obtained using SIPO machine translation system from SIPO CN, patent published Jun. 11, 2008.*

English langauge translation of CN 101118226 Ye et al., obtained using SIPO machine translation system from SIPO CN, patent published Feb. 6, 2008.*

Koo et al., U.S. Appl. No. 11/073,160, entitled "Sensor Arrays and Nucleic Acid Sequencing Applications", filed Mar. 4, 2005, 31 pages.

Su et al., U.S. Appl. No. 12/459,309, entitled "Chemically Induced Optical Signals and DNA Sequencing", filed Jun. 30, 2009, 45 pages.

Elibol et al., U.S. Appl. No. 12/655,578, entitled Nanogap Chemical and Biochemical Sensors', filed Dec. 31, 2009, 49 pages.

Liu et al., U.S. Appl. No. 12/823,995, entitled "Nucleotides and Oligonucleotides for Nucleic Acid Sequencing", filed Jun. 25, 2010, 50 pages.

Peng et al., "Polymerase-Directed Synthesis of 2'-Deoxy-2'-fluoro-β-D-arabinonucleic Acids", Journal of American Chemical Society, vol. 129, No. 17, Apr. 10, 2007, pp. 5310-5311.

Watts et al., "2'F-Arabinonucleic acids (2'F-ANA)—History, properties, and new frontiers", Canadian Journal of Chemistry, vol. 86, No. 7, Jul. 1, 2008 , pp. 641-656.

Bentley et al., "Accurate whole human genome sequencing using reversible terminator chemistry", Nature, vol. 456, Nov. 6, 2008, pp. 53-59.

Elibol et al., "Nanoscale thickness double-gated field effect silicon sensors for sensitive pH detection in fluid", Applied Physics Letters, vol. 92, No. 19, May 2008, pp. 193904-1 to 193904-3.

Gabig-Ciminska et al., "Electric chips for rapid detection and quantification of nucleic acids", Biosensors and Bioelectronics, vol. 19, 2004, pp. 537-546.

Guo et al., "Four-color DNA sequencing with 3'-O-modified nucleotide reversible terminators and chemically cleavable fluorescent dideoxynucleotides", Proceedings of the National Academy of Sciences (PNAS), vol. 105, No. 27, Jul. 8, 2008, pp. 9145-9150.

Kling, "Ultrafast DNA sequencing", Nature Biotechnology, Nature Publishing Group, vol. 21, No. 12, Dec. 2003, pp. 1425-1427.

Ronaghi et al., "DNA Sequencing: A Sequencing Method Based on Real-Time Pyrophosphate", Science Magazine, vol. 281, No. 5375, Jul. 17, 1998, pp. 363-365.

Seeberger et al., "2'-Deoxynucleoside Dithiophosphates: Synthesis and Biological Studies", Journal of American Chemical Society, vol. 117, No. 5, Feb. 1995, pp. 1472-1478.

Yeung et al., "Electrochemical Real-Time Polymerase Chain Reaction", Journal of American Chemical Society, vol. 128, No. 41, Sep. 23, 2006, 4 pages.

Chen et al., "Noncovalent functionalization of carbon nanotubes for highly specific electronic biosensors", Proceedings of the National Academy of Sciences (PNAS), vol. 100 No. 9, Apr. 29, 2003, pp. 4984-4989.

Gao et al., "Conferring RNA polymerase Activity to a DNA polymerase: A single residue in reverse transcriptase controls substrate selection", Proceedings of the National Academy of Sciences (PNAS), Biochemistry, vol. 94, Jan. 1997, pp. 407-411.

DeLucia et al., "An error-prone family Y DNA polymerase (DinB homolog from *Sulfolobus solfataricus*) uses a 'steric gate' residue for discrimination against ribonucleotides", Nucleic Acids Research, vol. 31. No. 14, 2003, pp. 4129-4137.

Star et al., "Electronic Detection of Specific Protein Binding Using Nanotube FET Devices", American Chemical Society, Nano Letters, vol. 3, No. 4, Mar. 5, 2003, pp. 459-463.

Elibol et al., "Localized heating and thermal characterization of high electrical resistivity silicon-on-insulator sensors using nematic liquid crystals", Applied Physics Letters, 93, Sep. 30, 2008, pp. 131908-1-131908-3.

Rolka et al., "Integration of a Capacitive EIS Sensor into a FIA System for pH and Penicillin Determination," Sensors, ISSN 1424-8220, Aug. 2004, 4, pp. 84-94.

Fritz et al., "Electronic detection of DNA by its intrinsic molecular charge", Proceedings of the National Academy of Sciences (PNAS), vol. 99, No. 27, Oct. 29, 2002, pp. 14142-14146.

Janicki et al., "Ion sensitive field effect transistor modelling for multidomain simulation purposes", Microelectronics Journal 35 (2004) pp. 831-840.

Zevenbergen et al., "Mesoscopic Concentration Fluctuations in a Fluidic Nanocavity Detected by Redox Cycling", American Chemical Society, Nano Letters, vol. 7, No. 2, 2007, pp. 384-388.

Office Action for U.S. Appl. No. 11/226,696, mailed on Jul. 24, 2007, 14 pages.

Response to Office Action for U.S. Appl. No. 11/226,696, filed on Dec. 21, 2007, 7 pages.

Office Action for U.S. Appl. No. 11/226,696, mailed on Mar. 14, 2008, 15 pages.

Response to Office Action for U.S. Appl. No. 11/226,696, filed on Jun. 19, 2008, 8 pages.

Office Action for U.S. Appl. No. 11/226,696, mailed on Sep. 17, 2008, 24 pages.

Response to Office Action for U.S. Appl. No. 11/226,696 filed on Dec. 17, 2008, 9 pages.

Office Action for U.S. Appl. No. 11/226,696, mailed on Jul. 14, 2009, 27 pages.

Response to Office Action for U.S. Appl. No. 11/226,696 filed on Nov. 16, 2009, 10 pages.

Office Action for U.S. Appl. No. 11/226,696, mailed on Mar. 9, 2010, 36 pages.

Response to Office Action for U.S. Appl. No. 11/226,696 filed on May 10, 2010, 13 pages.

Advisory Action for U.S. Appl. No. 11/226,696, mailed on May 17, 2010, 25 pages.

Notice of Non-Compliant amendment for U.S. Appl. No. 11/226,696, mailed on Feb. 26, 2009, 4 pages.

Response to Notice of Non-Compliant amendment for U.S. Appl. No. 11/226,696, filed on Mar. 26, 2009, 9 pages.

Response to Office Action for U.S. Appl. No. 11/967,600, filed on May 28, 2010, 12 pages.

Office Action for U.S. Appl. No. 11/967,600, mailed on Jan. 21, 2010, 10 pages.

Response to Office Action for U.S. Appl. No. 11/967,600 filed on Oct. 13, 2009, 7 pages.

Office Action for U.S. Appl. No. 11/967,600, mailed on Jun. 11, 2009, 12 pages.

International Search Report and Written Opinion for PCT Patent Application No. PCT/US2011/049605, mailed on Apr. 27, 2012, 9 pages.

* cited by examiner

ELECTRONIC AND FLUIDIC INTERFACE

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and is also related to U.S. patent application Ser. No. 11/967,600, entitled "Electronic Sensing for Nucleic Acid Sequencing," filed Dec. 31, 2007, now pending, and U.S. patent application Ser. No. 12/823,995, entitled "Nucleotides and Oligonucleotides for Nucleic Acid Sequencing," filed Jun. 25, 2010, now pending, the disclosures of which are incorporated herein by reference.

BACKGROUND OF THE INVENTION

1. Field of the Invention

Embodiments of the invention relate generally to fluidic interfaces for electronic sensors, electronic sensors for chemical and biochemical detection, arrays of electronic sensors, biomolecule detection, and nucleic acid sequencing.

2. Background Information

Molecular detection platforms that are miniaturized and manufacturable in high volumes, such as electronic sensors, offer the ability to provide access to affordable disease detection in places and situations in which such access was not in the past possible. The availability of affordable molecular diagnostic devices reduces the cost of and improves the quality of healthcare available to society. Affordable and or portable molecular detection devices also have applications, for example, in security and hazard detection and remediation fields and offer the ability to immediately respond appropriately to perceived biological, biochemical, and chemical hazards.

Electronic biochemical and chemical sensors have applicability in molecular diagnostics, substance detection and identification, and DNA detection and sequencing applications. Electronic bio/chemical sensors are manufacturable using semiconductor processing techniques. Sensors can be built on a surface of a silicon wafer that is diced up (cut apart) to make individual chips. Electronic sensors for bio/chemical applications can take a variety of forms, such as for example, the sensors can be electrodes, nano-gap electrodes, FETs (field effect transistors), extended gate FETs, carbon nano-tube transistors, and photon detectors.

One approach to disease detection in plants and animals involves analyzing sequence information for nucleic acid molecules such as deoxyribonucleic acid (DNA) and ribonucleic acid (RNA). The human genome contains approximately three billion nucleotides of DNA sequence and an estimated 20,000 to 25,000 genes. DNA sequence information can be used to determine multiple characteristics of an individual as well as the presence of and or suceptibility to many common diseases, such as cancer, cystic fibrosis, and sickle cell anemia. A determination of the sequence of the human genome required years to accomplish. The need for nucleic acid sequence information also exists in research, environmental protection, food safety, biodefense, and clinical applications, such as for example, pathogen detection, i.e., the detection of the presence or absence of pathogens or their genetic varients.

DETAILED DESCRIPTION OF THE INVENTION

Figure 1A:
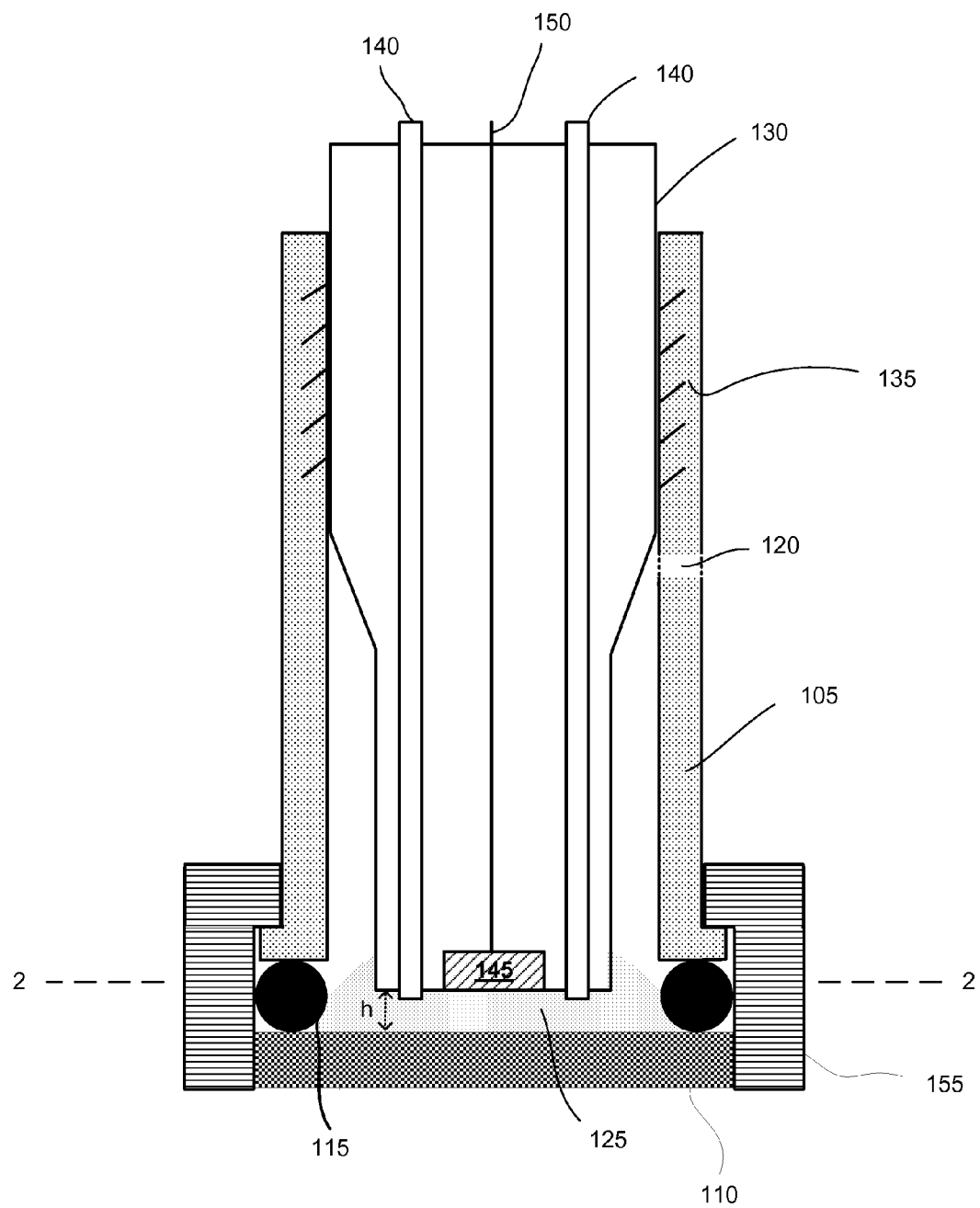
FIGS. 1A and 1B describe an electronic fluidic interface.

In electrical biochemical and chemical sensing there is a need to deliver fluid to the sensors while simultaneously making electrical connections to the sensor chip. Fluids such as the ones used in bio/chemical applications can cause chips to fail if the fluids come in contact with electronic components of the chip and the device in which the chip is housed. The failure of electronic devices is exacerbated by the salts contained in fluids. Nucleic acid sequencing applications such as, for example, the ones described herein, require the repeated delivery and removal of fluids to and from the sensing regions of a chip. The incompatibility of fluids with the electronic components associated with electronic sensor chips presents challenges to the design of a robust interface that allows the repeated delivery and removal of fluids to chips in a manner that is reproducibly robust and that also allows chips to be removed from and placed into the device.

Advantageously, in embodiments of the invention, fluid is capable of being exchanged onto and off of sensors rapidly. In embodiments, fluid is supplied to all the sensors at once. Further the amount of fluid supplied to the sensing regions of the chip for each reaction performed and or detected at the sensors is minimized, thus providing the advantage of conserving expensive reagents. Additionally, embodiments of the invention provide for turbulent mixing of fluids in the surface regions of the sensor chip. During solution addition turbulent mixing is important for washing unwanted reagents and products from the sensor surfaces and for mixing solutions of reagents that have been added to the sensing regions of the sensing chip.

Chips in the semiconductor industry are also known as microchips, integrated circuit (IC) chips, or dies. Sensing regions are located on a surface of the chip and are electronically coupled to other components. Other electronic components are optionally located in the interior of the chip or on the surface of the chip and enclosed with an inert insulating material. Typically, circuits allow the sensors to be addressed individually. Optionally, electronics for performing some or all of the functions of driving the sensors and measuring and amplifying events at the surface of the sensors are contained within the chip. After manufacture, the sensing chip is optionally packaged in a manner that takes into account the operating environment provided by the device in which the chip will reside. In general, the package for a chip protects the chip from damage and supplies electronic connections that connect the chip to power supplies and other electronic components (performing, for example, input/output functions) that make up the device in which the chip resides. The package may additionally contain multiple dies in a stacked or flip-chip configuration with optional discrete components making a complete system in package (SiP). Alternatively, the sensor chip is not packaged. For operation, the circuitry contained within the chip is electrically connected to additional devices that, for example, amplify and record signals, collect and analyze signal data, and provide power.

Figure 1B:
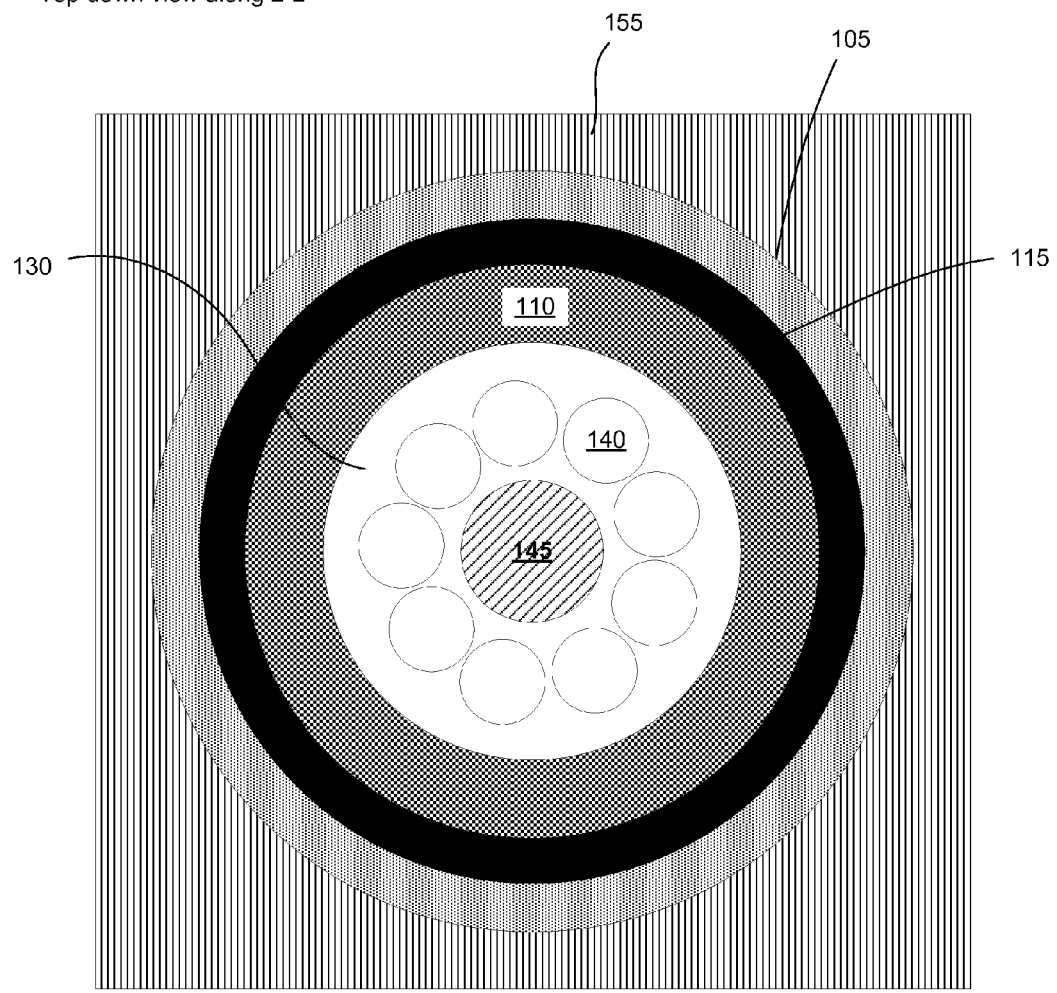

FIGS. 1A and 1B show an electronic and fluidic interface for a bio/chemical sensor chip. In FIG. 1A a cut-away view shows a fluidic interface to a sensor chip that is compatible with the electronics used to drive the chip. A housing 105 is intimately associated with the surface of a sensing chip 110 and a fluidic seal is formed between the housing 105 and the sensing chip 110 by the sealing member 115 located between the surface of the sensing chip and the housing 105. The sealing member 115 is typically comprised of a deformable polymer such as Teflon, Teflon coated rubber, Viton (a synthetic rubber fluoroelastomer), nitrile, silicone, polytetrafluoroethylene (PTFE), Neoprene (polychloroprene), and natural rubber. In this embodiment, the housing 105 has a cylindrical shape and the sealing member 115 is an o-ring. The sealing member 115 can be any shape that is capable of forming a fluidic seal between the chip and the housing 105. The fluidic seal is capable of preventing liquid movement across the seal at any pressure exerted through a line connected to an external pressure/vacuum source during operation of the device. Other shapes include ovals, squares, rectangles, and multisided figures, for example. The housing 105 optionally comprises one or more holes 120 that allow the chamber 125 to remain at or be placed at a selected pressure (such as, atmospheric pressure) during operation. In operation, chamber 125 contains fluid that is delivered through tube(s) 140. A plunger assembly 130 is placed inside of housing 105. The housing and plunger assembly are fabricated from materials such as, for example, ceramic, sapphire, metal alloys (stainless steel, titanium, bronze, copper, gold), or engineered plastics (Teflon, polyether ether ketone (PEEK), polyethylene). In some embodiments, plunger assembly 130 is removably attached inside housing 105. Optionally the plunger assembly 130 can screw into the housing 105 and screw threads 135 are provided inside housing 105 and in plunger assembly 130 (screw threads not shown). Other mechanisms for attachment are possible, such as, for example, retaining rings or clips. Attachment mechanisms exert pressure on the assembly to form a seal between the chip 110 and the plunger 130. In alternate embodiments the plunger assembly and the housing are one unit either, for example, because they have been mechanically attached, molded as one, or because they were machined from the same substrate.

The plunger assembly comprises at least one tube 140 that allows fluid to be delivered to and removed from chamber 125. The number of tubes 140 is dependent, in part, on the how the sensing chip 110 will function, the number of fluids that will be delivered to the sensors, the size of the tubes, and the size of the plunger assembly 130. In some embodiments, the number of tubes 140 is between 1 and 25 tubes. In other embodiments, a number of tubes 140 that is between 2 and 10 is used. In additional embodiments, there are at least two tubes 140. Separate tubes 140 are optionally used for fluid delivery and removal. One or more tubes 140 are optionally also used for maintaining the chamber 125 at a selected pressure. Tubes 140 are optionally microfabricated (or micromachined) holes in a solid plunger body. Alternately, the plunger body comprises a hole through which tubing is placed. In operation, one or more tube(s) 140 is fluidically connected to fluid reservoirs that hold fluids comprising reagents and other materials that are to be delivered to the sensing regions of the sensing chip 110 and one or more tube(s) 140 is connected to a source of a vacuum through tubing (not shown) that is connected to the tube(s) 140.

In some embodiments, the plunger assembly 130 is provided with an electrode 145 that is capable of functioning as a counter and or reference electrode and is electrically connected to the exterior of the plunger 150 and capable of being electrically coupled to electronics associated with driving the chip (not shown). The electrode 145 is comprised of a conducting material that is inert under reaction conditions chosen for operation of the device, such as, for example, platinum (Pt), gold (Au), palladium (Pd), nickel (Ni), copper (Cu), iridium (Ir), titanium (Ti), rhodium (Rh), as well as alloys of metals, conducting forms of carbon, such as glassy carbon, reticulated vitreous carbon, basal plane graphite, edge plane graphite, graphite, conducting polymers, metal doped conducting polymers, conducting ceramics, and conducting clays. The reference electrode is, for example, silver (Ag), silver/silverchloride (Ag/AgCl), platinum (Pt), saturated calomel (mercury-chloride), or other material and may be optionally enclosed in a glass or polymer housing which is semi-permeable to fluid.

Optionally a device (not shown) is supplied as part of plunger assembly 130 or the chip 110 that is capable of measuring the pressure inside chamber 125. Similarly a device (not shown) is supplied as part of plunger assembly 130 or the chip 110 that is capable of measuring the temperature inside chamber 125. In embodiments, plunger assembly 130 is provided with heating and or cooling elements (not shown).

Additionally optionally, one or more optical fibers is placed in the plunger assembly 130 to illuminate fluids in the chamber 125. An array of photon detectors is placed on the sensing chip 110 surface and optical properties are measured. Fluorescence spectroscopy, for example, is performed.

A retaining member 155 attaches the plunger assembly 135 to a substrate (not shown) that houses chip 110 (or to a substrate to which the housing for the chip 110 is attached) so that the sealing member 115 forms a fluidic seal that creates chamber 125 that is capable of retaining liquids. In the present embodiment, the sealing member 115 is in intimate contact with sensing chip 110. In alternate embodiments, the sealing member 115 is in contact with the packaging substrate (not shown) surrounding sensing chip 110 on which the sensing chip 110 has been mounted. The sensing chip 110 is either packaged in a manner that leaves the sensing elements exposed or it is not packaged.

In general, the chamber 125 is large enough to allow turbulent mixing to occur within the chamber 125. Maintaining atmospheric pressure can relieve the effects of pressure fluctuations on the sensor response that can occur when fluid is flowing. The chamber shown in FIG. 1A typically has a diameter of between 100 µm and 10 cm, between 1 mm and 8 cm, and between 1 cm and 5 cm. The diameter selected is in part, a function of the size of the sensing chip. The height of chamber 125 (labeled "h" in FIG. 1A), is in the range of 100 µm to 10 cm. The height selected depends, in part, on the number of fluids being added to the chamber 125 and the rate of fluid injection into the chamber 125. In general the chamber 125 holds a volume of liquid that is in the range of 100 nL to 1 mL. The grey area in FIG. 1A demonstrates the positioning of fluid in chamber 125. The grey area provides an approximate indication of how much fluid is in chamber 125 during operation of the sensing chip and or during washing of the sensing chip surface, although amounts that are larger or smaller are also possible.

FIG. 1B provides a top-down view along the line 2-2 of the device shown in FIG. 1A. In FIG. 1B, the housing 105 encloses the sealing member 115. The top-down view of FIG. 1B allows the sensing chip 110 to be seen through the space between the plunger assembly 130 and the housing 105. Plunger assembly 130 houses tubes 140 and optionally an electrode 145. Although eight tubes 140 are shown, other numbers of tubes 140 are also possible, as mentioned above, such as, for example, from 1 to 25 tubes. The retaining member 155 is shown as having a square contour in the cut-through view of FIG. 1B, however other shapes are possible, such as larger, more complex, and or elongated shapes that serve to protect underlying electronics from fluids that are delivered to the plunger assembly 135 during device operation. In general, retaining member 155 is a part that is adapted to hold the plunger assembly 130 in place. Other configurations for retaining member 155 are possible.

Figure 2A:
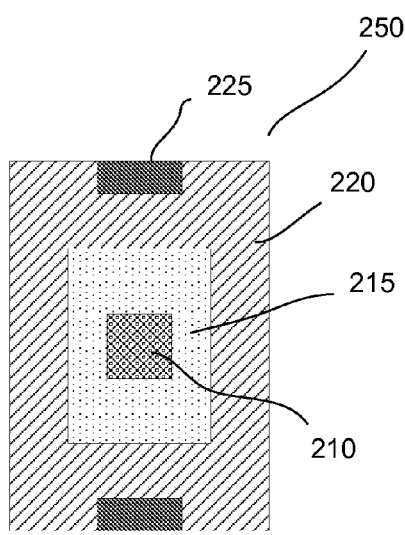
FIGS. 2A and 2B provide views of an electronic sensor chip assembly.

FIG. 2A depicts a chip assembly 250 that is useful in conjunction with the electronic and fluidic interface of FIGS. 1A and 1B. In FIG. 2A sensing chip 210 is mounted on and electrically connected to socket 215 that provides an electronic interface (not shown) between the chip 210 and the external electronics (not shown) that drive the sensor chip 210 and measure and record information from the chip 210. In this embodiment the chip 210 has been flip-chip (or wire) bonded to the socket 215 and the electronic interface sealed with a protective fluid-resistant material such as, epoxy, polyimide, or other polymer. The chip 210 can be bonded in general to any substrate that has larger leads for making connections (such as a printed circuit board (PCB)). Other configurations for the electronic connection of the chip are possible, such as for example, the sensor chip can be attached to a packaging substrate that provides electronic connections. The socket 215 is made of, for example, a machinable polymer, and it has metal pins that are capable of making a connection to the pads on the chip and interfacing to external electronics. The socket 215 holds the chip 210 and provides fixed electrical leads designed to fit the chip. In embodiments, the chip 210 does not permanently attach to the socket 215 and the socket 215 does not provide physical support to fix the chip. In other configurations such as using a PCB, physical supports are provided for the chip 215 that guide and maintain its placement in a certain location. The packaging substrate comprising the chip (or unpackaged chip itself) optionally is then detached from the chip assembly so that a new or different packaged or unpackaged chip can be placed in the chip assembly. In the case of the packaged sensor chip, the sensor chip is electrically connected to the package substrate which is then optionally electrically connected to an electronic interface that interfaces between the electronics that supply power to the sensor chip, drive the sensor chip, and or measure and or record and or analyze information from the chip.

Alternatively, the chip is provided with external electrical connection points on the periphery of the chip and the connection points from the chip are attached to the electrical connection points in the socket. In further alternate embodiments, the chip has external electrical connection points located at the periphery of the chip which are wire bonded to leads in the socket. Additionally, the chip may also have sensors located on one face of the chip and external electrical connection points located on the opposite face of the chip. In this case the whole area at the bottom of the chip can be used for electrical connection, and technologies such as a ball grid array are used. Also, multiple die can be packaged together to build a complete system in package (SiP) in either a stacked or flip chip configuration, for example.

The socket 215 is housed in substrate 220 that has clips 225 that attach the chip assembly to the device that houses the fluidic interface. In general, other configurations are possible that allow the sensor chip to be removably associated with the fluidic interface, such as ones that allow the holder comprising the chip to be slid out of the device and a new or different chip to be placed in the device. Once the chip is placed in the device, a fluidic seal is formed between the fluidic interface and the surface of the chip that comprises the electronic sensors. In alternate embodiments, the chip is removably placed in a PCB that provides electronic connections that are aligned to the pads on the die so that the die and PCB are placed face to face and the PCB is cut in a way to expose areas which contains the sensors on the die.

Figure 2B:
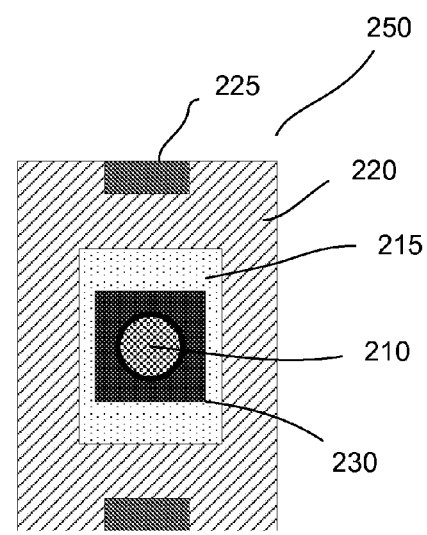

FIG. 2B shows the chip assembly of FIG. 2A also including a sealing member 230. In alternate embodiments, the sealing member 230 is provided with the chip assembly rather than attached to the plunger housing. Although sealing member 230 is shown in this embodiment as having a square outline and a cut-out interior circle, other shapes are possible, such as, for example, ring, oval, square, rectangular, and multi-sided (three or more sides) for either or both the interior and exterior profiles. The shape chosen for the sealing member 230 allows it to provide a fluidic seal between the housing and the surface of the sensor chip.

Figure 3A:
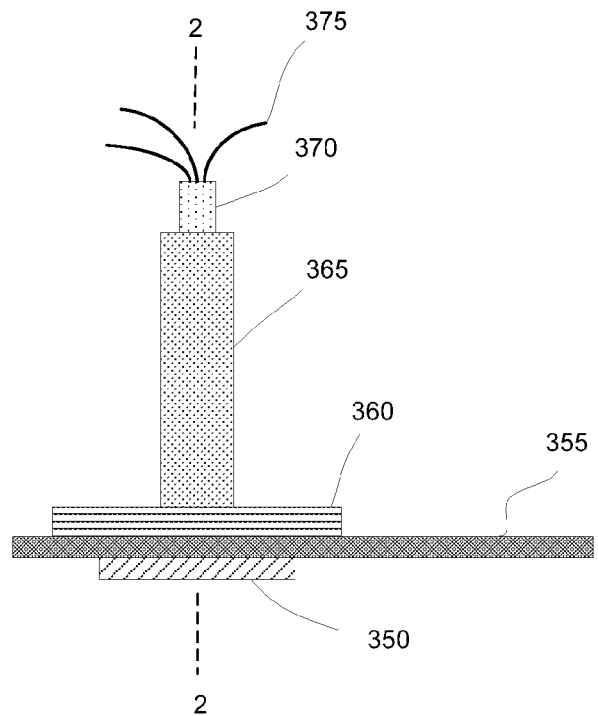
FIGS. 3A and 3B show a device that is made up of an electronic sensor chip assembly and fluidic interface that provides both an electronic and a fluidic interface for a sensor chip.

FIG. 3A shows a chip assembly such as those of FIGS. 2A and 2B associated with a fluidic interface. In FIG. 3A, the chip assembly 350 is removably attached to a face of substrate 355. The sensor chip (which is not shown in FIG. 3A), faces a hole in substrate 355. The substrate is comprised of, for example, silicon, quartz, glass, polymer, PCB (polychlorinated biphenyl) materials. The fluidic interface for the sensor chip is attached to the opposite side of substrate 355 and is in fluid communication with the sensor chip through a hole in substrate 355. The fluidic interface comprises retaining member 360 that holds the housing 365 and the plunger assembly 370 that is located inside the housing 365 in place. Optionally, the retaining member 360 and the housing 365 are one unit or alternatively, the retaining member 360 is bonded or mechanically attached to the housing 365 forming a fluidic seal that prevents unwanted fluids from reaching the substrate 355 that may house electronics or reaching any other nearby electronic components. The housing 365 is fluidically associated through the hole in the substrate 355 with the sensor chip and there is a fluidic seal between the surface of the sensor chip and the housing 365. A plurality of tubes 375 connect the plunger assembly 370 to fluid reservoirs (not shown) and to a vacuum supply (not shown). Optionally, a tube 375 is used to maintain a desired pressure, such as atmospheric pressure, in the device during operation, such as when the chamber is being filled with fluids and while the chamber is filled with fluids. The number of tubes 375 depends in part on the functionality desired for the chip. The tubes 375 extend all the way through the plunger assembly 370 or are attached holes (not shown) in the interior of plunger assembly 370.

Figure 3B:
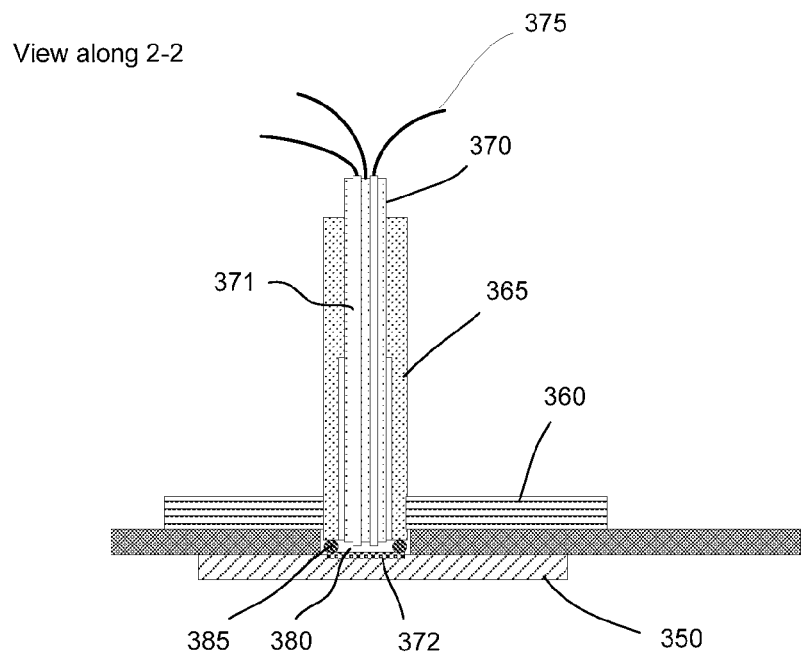

FIG. 3B provides a cut-away view along line 2-2 of FIG. 3A. In FIG. 3B, the chip assembly 350 is removably attached to a face of substrate 355. The sensor chip 372 faces a hole in substrate 355. The fluidic interface for the sensor chip 372 is attached to the opposite side of substrate 355 and is in fluid communication with the sensor chip through the hole in substrate 355. The fluidic interface comprises retaining member 360 that holds the housing 365 in place and the plunger assembly 370 that is located inside the housing 365. Plunger assembly 370 is optionally removably attached inside housing 365 through mechanical means, such as screw bores or retaining clips. Removable attachment allows plunger assembly 370 to be removed for cleaning. Plunger assembly 370 has one or more hole(s) 371 through which fluid is capable of traveling (or tubing can be placed). Optionally tubing 375 extends through hole(s) 371 or is attached to (or in) hole(s) 371. With the attachment of the fluidic interface and the chip assembly 350 to the substrate 355, the hole in the substrate 355 becomes chamber 380. A sealing member 385 fluidically seals the housing 365 to the surface of the sensor chip 372. Optionally, the sealing member 385 is attached to the housing 365 so that it remains in place when the chip assembly 350 is removed. Optionally, an electrode (not shown) that is facing the chamber 380 and that is capable of serving as a counter electrode is present in the plunger assembly 370. An electrical connection is provided from the electrode to the exterior of the housing and or plunger assembly so that the electrode is in electrical communication with outside electronics. Optionally, housing 365 has a hole (not shown) that allows the chamber 380 to be maintained at atmospheric pressure (or other pressure). Additionally optionally, an optical fiber is placed in the plunger assembly 370 to illuminate fluids in the chamber 380. An array of imaging sensors (photon detectors) is placed on the sensing chip surface and optical properties are measured. Fluorescence spectroscopy, for example, is performed.

Specific embodiments are provided in which electronic fluidic interfaces are used in DNA sequencing applications. The electronic fluidic interfaces provided, however, are useful generally in applications in which a fluidic interface is formed with an electronic sensing chip. The electronic sensing chip is capable of performing analysis on the contents of the fluid.

Figure 4:
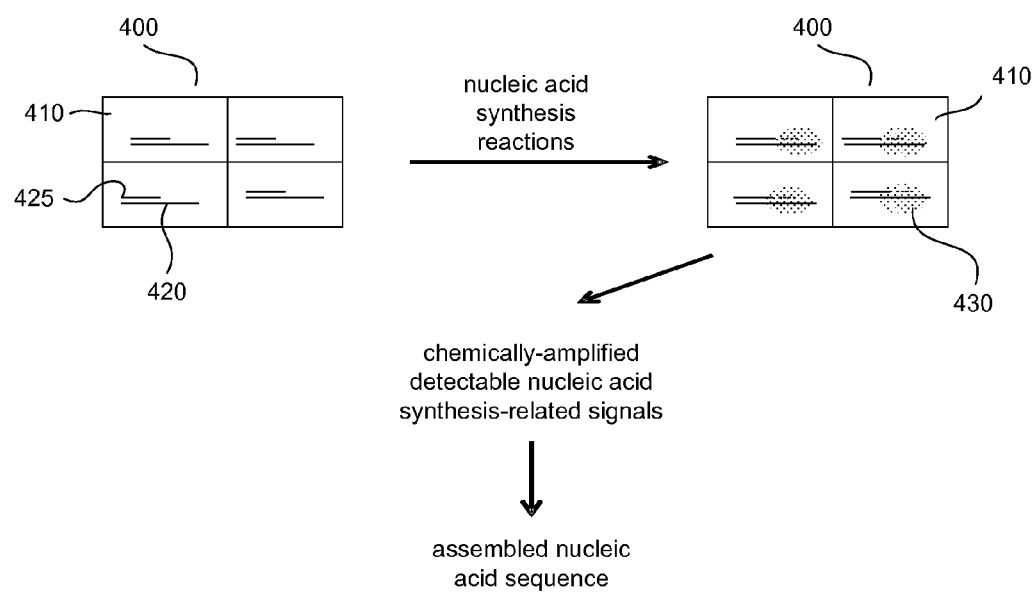
FIG. 4 provides a simplified array of electronic sensors that function as detectors for nucleic acid sequencing reactions.

FIG. 4 provides an array of electronic sensors that function as nucleic acid sequencing sensors. In FIG. 4, an array of electronic sensors 400 having reaction and detection regions 410 and immobilized DNA molecules 420 is shown. The electronic sensors 400 are, for example, field effect transistors (FETs), extended gate FETs, and or electrodes. In this example, the detection region 410 is the region proximate to the surface of the sensors 400 in which the sensors 400 are capable of detecting changes in a solution that is in contact with the sensors. One DNA molecule to be sequenced is immobilized per detection region 410 in this embodiment, although more than one DNA molecule (that are copies of the same molecule) are optionally immobilized in the sensor region also. Optionally, the detection regions 410 are formed in depressions or wells in a substrate surface. In embodiments of the invention one DNA molecule is immobilized in the detection region 410. In other embodiments of the invention, a plurality of molecules are immobilized. Before sequencing a sample of DNA, overlapped DNA fragments are immobilized randomly on the surface of a substrate so that statistically one DNA molecule 420 occupies the reaction and detection region 410.

A sample of DNA is optionally fragmented into smaller polymeric molecules using, for example, restriction enzymes or mechanical forces (shearing). The immobilized nucleic acid is primed with a primer 425 that is terminated with a nuclease resistant base and nucleic acid synthesis and deconstruction reactions are performed and amplified chemical products of the synthesis reactions 430 are created in the detection regions 410. The detection of reaction products indicates the identity of the next complementary nucleotide. The identified base position is then filled with a matching known nuclease resistant nucleoside polyphosphate (that is optionally a reversibly blocking nucleoside that is capable of preventing the further addition of nucleosides), and the reaction is repeated to determine a matching base for the next available position on the DNA strand 420. These elements of the method (identification of a base position and filling the position with a nuclease resistant blocking version of the matching nucleotide that has been determined by the identification reaction) are repeated to determine sequence information for the surface-attached DNA strand 420. The number of times the reaction is repeated depends in part on the number of bases of DNA to be sequenced.

In FIG. 4, the amplified chemical products 430 are detected electronically and sequence data for the immobilized DNA molecules are assembled. Amplified chemical products in a reaction and detection region 410, such as, for example, a gate of a FET, alter the current flow and capacitance between the source and the drain of the FET allowing electronic detection of the chemically amplified products of the nucleic acid synthesis reactions. Detected reaction products and their corresponding positions in the array are recorded and analyzed using a computer and analysis software or embedded firmware on the chip. The detection of chemical changes within the sensor is performed in real time as concentrations of enzymatic products increase or at the end of the reactions. Data from regions having no immobilized nucleic acid sample or a plurality of immobilized samples are distinguished. Additionally, a computer is optionally used not only to direct the addressing and monitoring of the reaction regions of the array, but also to provide reagents to the array from fluidically coupled reservoirs through an electronic fluidic interface. Additionally, a computer analyzes data and assembles sequence information. The detection of chemical changes within the sensor is performed in real time as concentrations of enzymatic products increase or at the end of the reactions.

Electronic sensors are monitored individually or as a group. The sensor array allows, for example, many immobilized DNA molecules to be sequenced simultaneously through the monitoring of individual reaction regions. The immobilized DNA molecules can either be a sample to be sequenced or capture DNA probes of known sequence can be first immobilized and then the sample to be sequenced can be hybridized to the immobilized probes. The capture probes have a sequence designed to hybridize to complementary sections of the sample DNA. In some embodiments, DNA molecules to be immobilized are diluted so that statistically each sensor has one DNA molecule immobilized. Nucleic acid sequencing is sometimes performed on a sample containing long polymers of nucleic acids. The sample is prepared by cutting the long polymers into smaller polymers of 50 nucleotides in length or less. Cutting long DNA polymers is done, for example, using a restriction enzyme or through shearing using mechanical forces. The smaller single-stranded nucleic acid polymers are then immobilized in the cavity of an electronic sensor. Information from electronic sensors showing ambiguous results is disregarded. Sequence information from individual DNA molecules is stitched together to create the sequence of the longer polymeric DNA that was broken into smaller polymers.

In additional embodiments, multiple molecules of the same sequence are used in one sensor. The attachment of many DNA molecules having the same sequence in a sensor region is accomplished for example, by attaching a carrier containing many DNA molecules of the same sequence onto a sensor region, using, for example, emulsion polymerization techniques. Emulsion polymerization amplifies DNA molecules inside water bubbles surrounded by oil. The water bubbles contain a single primer-coated bead and a single initial DNA molecule that attaches to the bead and is amplified by enzymes in the water bubble. The bead becomes the carrier of an amplified sequence of DNA. The DNA molecule to be sequenced can also be amplified in situ after attachment to the sensor region. Additionally, the DNA molecule can be amplified using rolling circle amplification forming one long molecule having many repeats of the same sequence.

In FIG. 4, an array comprising four sensors is shown for simplicity. Arrays of electronic sensors fabricated using semiconductor processing techniques can contain many more individually addressable sensing regions per sensing chip. The selection of the number of sensing units depends on factors such as cost, accuracy desired (e.g., for more accurate sensing redundant sensor reactions are employed), and number of different types of molecules to be detected. Although, sensing chips (devices) comprising one sensing region are also possible. In general, arrays of sensors are formed in a pattern or a regular design or configuration or alternatively are randomly distributed sensors. In some embodiments, a regular pattern of sensors are used the sensors are addressed in an X-Y coordinate plane. The size of the array will depend on the end use of the array. Sensor arrays allow many reaction sites to be monitored simultaneously. Arrays containing from about two to many millions of different discrete sensors can be made. Very high density, high density, moderate density, low density, or very low density arrays are made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

Standard silicon and semiconductor processing methods allow a highly integrated sensor array to be made. For example, a 1 cm$^2$ silicon wafer chip can hold as many as 1×10$^8$ sensor regions having an area of about 1 μm$^2$ and, a 2.5×5 cm$^2$ silicon wafer chip can hold as many as 5×10$^9$ sensors that occupy an area of about 0.5×0.5 μm$^2$.

In embodiments of the invention, electronic sensors are arrays of individually-addressable sensors. Arrays are built having a variety of dimensions and numbers of electronic sensor regions. The selection of number layout of sensors is informed by factors such as, for example, the types of analytes to be detected, the size of the sensing regions, and costs involved in manufacturing the arrays. For example, arrays of sensors are 10×10, 100×100, 1,000×1,000, 10$^5$×10$^5$, and 10$^6$×10$^6$.

Electronic sensors include devices such as, FET (field effect transistor) devices, extended gate FETs, electrodes for impedance detection and or redox detection, interdigiteted or closely spaced electrode configurations for redox cycling detection, and materials whose electrical properties are modulated by chemicals of interest (including certain polymers), and photon detectors. Electronic sensors employing electrodes are capable of measuring the impedance, the resistance, the capacitance, and or the redox potential of the materials that are located on or near the electrode surface. Electronic sensors employing photon detectors are capable of measuring decay lifetime of fluorescent tagged molecules using fluorescence spectroscopy.

Figure 5:
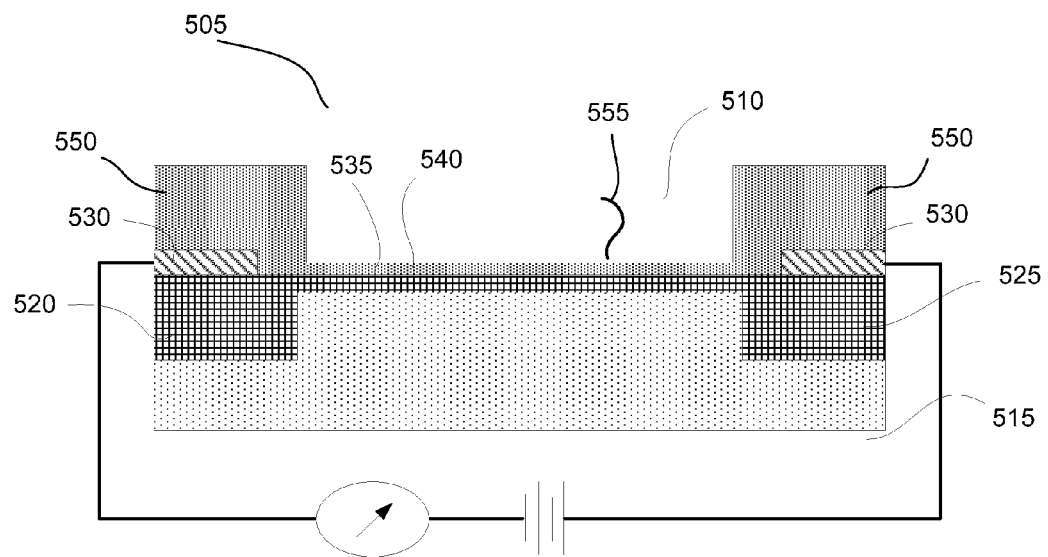
FIG. 5 shows a field effect transistor sensing device.

FIG. 5 shows a basic FET (field effect transistor)-based device 505 that is capable of sensing changes in a solution to be analyzed (not shown) that is placed in the optional device well 510 (or changes in proximate molecules for sensors having surface-attached species to be measured). The amplified chemical signals created in the well 510 from the nucleic acid synthesis reactions are converted into an electronic signal by the electronic sensor 505. The sensor 505 can be a P-type FET, a N-type FET, a carbon nanotube transistor, or a graphite transistor. In one embodiment, the sensor 505 has a nano-sized reaction well 510 and a semiconductor transistor that are separated by an insulating layer. The FET-based device 505 comprises a substrate 515, a source 520, a drain 525, conducting electrodes 530 (made of a metal such as, for example, gold, copper, silver, platinum, nickel, iron, tungsten, aluminum, or titanium metal), and a sensing region 535. The sensing region 535 (or the "channel") is typically comprised of a doped semiconductor material coated with a thin layer of insulating material 540 (such as, for example, silicon dioxide, silicon nitride, aluminum nitride, and or silicon oxynitride). The channel 535 of the semiconductor transistor, for example, can be comprised of a P- or N-type semiconductor, as is well known in the art, such as for example, silicon or germanium doped with boron, arsenic, phosphorous, or antimony. Optionally, the well 510 has dimensions of less than about 100 nm, less than about 1 μm, or less than about 10 μm. In general, in a FET, the electric field created by materials located in proximity to the sensing region 535, such as a solution in the well 510 and or materials attached directly onto the insulating material 540, change the conductivity of the sensing channel 535. Measurement of changes in the conductivity of the sensing channel 535 indicate changes have occurred in the materials that are proximate to the sensing channel 535, such as a reaction solution. Optionally, the biosensor comprises a well 510 created by surrounding inert sides 550, comprised, for example, of silicon dioxide, in which reagents and or products are contained. In alternate embodiments, sensors and arrays of sensors comprise a flat surface instead of a well or depression for the sensing region. Also optionally, a nucleic acid 555 or other molecule to be analyzed is attached above the sensing region 535. In other embodiments, the nucleic acid or other molecule to be analyzed is attached to, for example, a surface located above the sensing region 535 or on a side wall of the well. Advantageously, sensors designed so that they collect molecules to be detected near the sensing region, provide large enhancements in detection sensitivity over sensors that detect molecules that are in a solution. Examples include surface-attached specific binding molecules, molecules that specifically bind a target molecule of interest, such as pyrophosphate or phosphate binding molecules that are capable of specifically recognizing and binding pyrophosphate or phosphate ions.

Additionally the sensors are micro-fabricated metal electrodes made up of a metal in which the electrode metal is deposited on top of a channel region of an FET. In this instance the metal electrode becomes the extended gate of the FET device. The metal of the extended gate has a surface area that is functionally connected to a region where a biochemical (sequencing) reaction takes place. An extended gate FET has a metal that is functionally connected to a FET device that is made by, for example, CMOS process. The metal extended gate can be built in a process similar to the process used to build the interconnects on top of silicon substrate where FET sensors are located. The exposed surface of the extended gate is made of electrochemically stable noble metals, such as, Au, Pt, or Pd.

Figure 6:
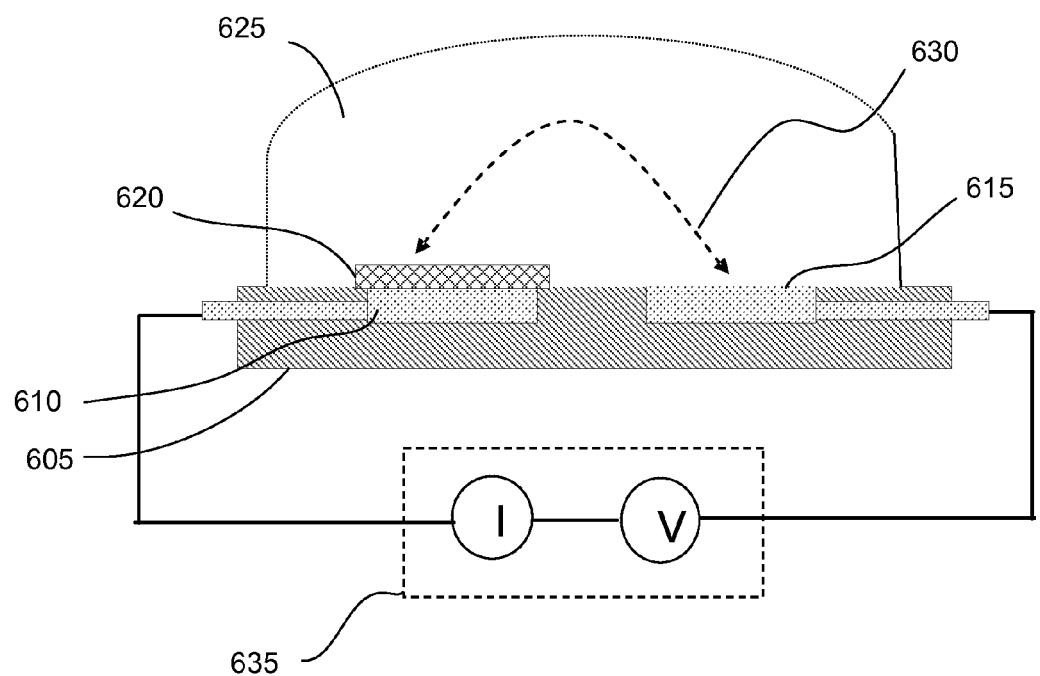
FIG. 6 shows an electronic sensor that employs electrodes as sensing elements.

Electrodes are used to measure the impedance (for AC current), the resistance, and or the capacitance of a solution to which they are exposed. In some instances the current at an electrode is measured as a function of applied DC voltage at the electrode-solution interface. Typically, impedance measurements involve measuring the electrical impedance at the electrode-solution interface under AC steady-state conditions and in the presence of a constant DC bias. FIG. 6 provides an exemplary biosensor in which an electrode provides the sensing element. In FIG. 6, a substrate 605 houses a first electrode 610, that functions as the working electrode, and a second electrode 615, that functions as the counter electrode. Additionally, a third electrode (not shown), an electrode that functions as a reference electrode optionally is also used. A reaction liquid 625 provides an electrical connection between the working electrode 610 and the counter electrode 615. The molecule(s) to be analyzed (not shown) are attached to the substrate 605, to the working electrode 610, or to another structure (not shown) that forms part of a working sensor device (such as, for example, the walls of a well surrounding the electrodes, or a microfluidic channel) so that the molecules to be analyzed are in solution and proximate to the electrodes. Optionally, a layer of molecules 620 to be detected (specific binding molecules, molecules that specifically bind a target molecule of interest, such as pyrophosphate or phosphate binding molecules that are capable of specifically recognizing and binding pyrophosphate or phosphate ions) is located above the working electrode 610. A hatched arrow 630 shows the movement of current or charge between the electrodes 610 and 615. An electronic circuit 635 measures impedance, capacitance, and or resistance. Typically, the current is detected under varying conditions. The output signal detected from the circuit 635 differs based on the input signal provided to the circuit 635. The input signal differs primarily in frequency and wave shape. Impedance, capacitance, and resistance are calculated based on detected current (I) under a given voltage (V) and frequency. The values calculated depend on the circuit model used. See, for example, Daniels, J. S., Pourmand, N., *Electroanaylsis*, 19, 1239-1257 (2007), Carrara, S., et al., *Sensors & Transducers Journal*, 88, 31-39 (2008), Carrara, S., et al., *Sensors & Transducers Journal*, 76, 969-977 (2007), and Wang, J. Carmon, K. S., Luck, L. A., Suni, I. I., *Electrochemical and Solid-State Letters*, 8, H61-H64 (2005). Optionally the circuit 635 is an integrated circuit. Electronics providing input and output control (not shown) are optionally housed in the substrate, such as in an integrated circuit chip, and or are provided through circuitry that is external the substrate.

Electrodes used in electronic sensing applications are comprised of a conducting material that is selected to be inert under reaction conditions, such as for example, gold or platinum. In further embodiments the electrodes made from metals, combinations of metals, or other conducting materials. For example, an electrode may be made from, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. The electrode surface is optionally modified, such as for example, through the silanation of the surface as a mechanism to facilitate coupling of molecules (analytes) to the surface of the sensor.

Electronic sensors are fabricated using, for example, integrated circuit (IC) processes (for example, CMOS, Bipolar, or BICMOS processes) used for chip manufacture. Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. The micromechanical components are fabricated using compatible micromachining processes that selectively etch away parts of the silicon wafer or add new structural layers to form the mechanical and/or electromechanical components. Electronic sensors are reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications. Because the electronic sensor can be very small and very sensitive, they provide the ability to detect molecules and biomolecules at ultralow concentrations.

Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Optionally some or all of the electronics for sensing and driving electrodes and recording data are integrated circuits that are part of the substrate that house an array of electronic sensors. Electronics providing input and output control are optionally housed in the substrate, such as in an integrated circuit chip, or are provided through circuitry that is external the substrate. An array of sensing electrodes is optionally equipped with circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and or field effect transistors (direct and floating gate). The chip also optionally includes embedded software (firmware) that manage some chip functions. One or more of the sensing functions can be performed by external instruments and or attached computer system.

Optionally, the sensor device additionally comprises heating and or cooling elements that are capable of controlling the temperature of the sensing region. Optionally sensor devices are electronically coupled to electronic circuitry for signal detection and thermal control. Thermal elements are optionally located within the sensing device, within the housing of sensing device, or in the electronic fluidic interface. Exemplary methods of controlling the temperature of the sensor device include using thin metal films of Au, Ag, or Pt as resistive heaters and using a separate metal film (Pt or Au) as a temperature sensor to provide temperature feedback to the control circuitry. Electronic circuitry couples the sensing device to computing elements capable of running control software and provides for drive power inputs for the sensors, signal detection, and thermal control.

A molecular attachment site on a sensor is a surface-attached chemical functional group or molecule that allows the addition of a monomer, linker, nucleic acid, protein, or other molecule to the surface of a substrate. The molecular attachment site comprises, in some embodiments, a reactive functional group that allows molecular addition or coupling. The molecular attachment site may be protected or unprotected. Sensor surfaces are functionalized, for example, with one of or a combination of amine, aldehyde, epxoy, and or thiol groups, and molecules to be attached are functionalized with amine (for surface bearing carboxy, epoxy, and or aldehyde functional groups) and carboxyl (for surface bearing amine groups), thiol (for surface of gold) to create molecular attachment sites. Various conjugation chemistries are available to join the functional groups. The concentration of molecules on the substrate surface is controlled, for example, in several ways: by limiting the density of surface functional groups or by limiting the quantity of molecules to be attached. In some embodiments, a molecular attachment site is a biotin molecule and the molecule to be attached is coupled to an avidin (or streptavidin) molecule.

Nucleic acid attachment sites are sites on a substrate surface that present functional groups, nucleic acids, affinity molecules, or other molecules that are capable of undergoing a reaction that attaches a nucleic acid to a substrate surface. DNA molecules are immobilized on a substrate or sensor surface by standard methods, such as, for example, through biotin-avidin or antibody-antigen binding. Biotin, avidin, antibodies, or antigens are attached, for example, to an insulating layer comprised of silicon oxide through derivatization of the silica surface with, for example, (3-aminopropyl)triethoxysilane to yield a surface that presents an amine group for molecule attachment. Molecules are attached by using water-soluble carbodiimide coupling reagents, such as EDC (1-ethyl-3-(3-dimethyl aminopropyl)carbodiimide), which couples carboxylic acid functional groups with amine groups. DNA molecules bearing a corresponding coupling group are then attached to the surface through, for example, a biotin-avidin or antibody-antigen interaction. Additionally, acrydite-modified DNA fragments are attached, for example, to a surface modified with thiol groups, and amine-modified DNA fragments are attached, for example, to epoxy or aldehyde modified surfaces. The nucleic acid attachment site is also a nucleic acid that is capable of hybridizing a nucleic acid to be attached to a surface.

Many substrate and electrode materials, such as metals, metal oxides, and $SiO_2$, have surface-attached —OH groups that are available for further reaction and molecular coupling. Further, surfaces that present —OH groups for molecular coupling are optionally created on substrate surfaces, through, for example, creating a thin oxide layer on a metal (such as through chemical or plasma etching processes) or through depositing a thin layer of $SiO_2$ onto the surface. If the substrate surface is $SiO_2$, the surface has been coated with $SiO_2$, or the surface is a metal having available —OH groups, molecules are optionally attached to the sensor surface through the use of silane linkers (organo silane compounds). Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules.

The density of attached molecules on a substrate surface is optionally controlled by providing blocking groups, i.e., groups that are not able to attach or bind a molecule along with the molecules that bind other molecules, such as for example, bovine serum albumen protein or non-functional silane molecules (molecules capable of silanating a silicon dioxide surface, but that do not present a functional group for further molecular attachment), on the surface for molecular attachment. By controlling the concentration of blocking and non-blocking molecules in the solution used to coat the surface for DNA binding, a statistically one DNA molecule is bound in the sensing region for detection. If the DNA is bound to the surface through a biotin-avidin interaction, the biotin-labeled DNA can be presented to the surface for attachment in a solution that also contains free biotin in a concentration to statistically end up with one DNA molecule in a cavity.

Figure 7:
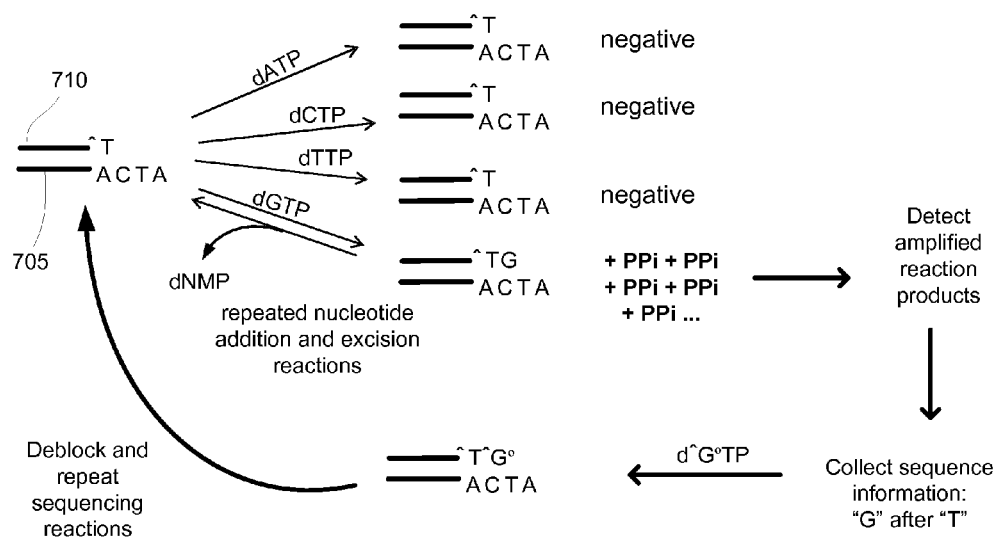
FIG. 7 outlines a general nucleic acid sequencing strategy in which electronic sensor chips and electronic fluidic interfaces are useful.

FIG. 7 diagrams a method for providing amplified chemical signals and sequencing data for nucleic acid sequencing reactions. The method shown in FIG. 7 is useful for sequencing segments of a DNA molecule using arrays of electronic detectors and an electronic fluidic interface. In FIG. 7, a DNA molecule to be sequenced 705 is primed with a primer 710 that is terminated with an exonuclease resistant nucleotide which, in this example, is a thymine (nuclease resistance being indicated in FIG. 7 with a "^"). The chemical products resulting from the incorporation of a complementary dNTP (a deoxynucleotide triphosphate, e.g., dATP (deoxyadenosine triphosphate), dCTP (deoxycytidine triphosphate), dGTP (deoxyguanosine triphosphate), or dTTP (deoxythymidine triphosphate), for example) or dNTP analog, that is complementary to a base of the nucleic acid strand to be sequenced 705 are amplified through the repeated addition and excision of the next complementary nucleotide onto the priming sequence 710. In one embodiment, individual test reactions are performed using one of four dNTPs and a determination is made regarding the next complementary nucleotide in the nucleic acid to be sequenced. In general, a test reaction comprises a polymerase, an exonuclease, and a deoxynucleoside triphosphate (such as dATP, dCTP, dTTP, or dGTP), a nucleoside oligophosphate comprising from 4 to 5 phosphates, or a labeled nucleoside analog (a labeled nucleoside tri- or oligophosphate comprising from 4 to 5 phosphates). Labels include redox labels that are redoxigenic, such as aminopheny, hydroxyphenyl, or napthyl groups attached to a terminal phosphate of the nucleoside tri- or oligophosphate that become redox active after the removal of phosphate groups. In general, a redoxigenic label is a label that becomes redox active after its removal from the polyphosphate nucleoside upon the incorporation of the labeled nucleoside into a nucleic acid molecule and can be detected at an electrode. The redoxigenic label undergoes further reaction after incorporation-related cleavage from the nucleoside polyphosphate, such as the removal of phosphate or pyrophosphate groups, before becoming redox active. After incorporation of the redox labeled nucleoside polyphosphate, phosphate groups are removed from the label using a phosphatase enzyme. The released redoxigenic label is detected electrochemically and or using redox cycling techniques.

In FIG. 7, a complementary nucleoside is incorporated into and excised from the growing DNA molecule (primer strand) 710 through the action of a polymerase enzyme. Typical useful polymerase enzymes include DNA polymerases, such as for example, *E. coli* DNA polymerase I and the commercially available 9 N and its modified derivatives such as, Therminator DNA polymerases (available from New England Biolabs, Inc., Ipswich, Mass.). Where there is a cytosine, for example, on the strand to be sequenced 705, a guanine will be incorporated, where there is a thymine, an adenosine will be incorporated, and vice versa. If the nucleoside triphosphate is incorporated into the growing strand 710 in the test reaction, then a pyrophosphate ion (i.e., a pyrophosphate, PPi, or $P_2O_7^{-4}$), polyphosphate, or labeled poly- or pyrophosphate is released. In an amplification reaction, an exonuclease is used to remove the incorporated nucleoside monophosphate ($dNMP^{-2}$), allowing another complementary nucleoside triphosphate to be incorporated and additional PPi to be released. Repetition of these addition and excision reactions provides amplification of the reaction products of nucleic acid synthesis. Thus, a positive test reaction (i.e., the detection of chemically amplified products) indicates that the base on the template DNA strand to be sequenced 710 immediately after the priming base (the 3' base) of the primer strand 710 is complementary to the test base (the one of four dNTPs that was used in the synthesis and deconstruction reaction). These elements of addition and excision are repeated at least until a detectable signal is realized. Optionally, the reaction sequence can be terminated when a positive result is obtained indicating the incorporation of a dNTP, without testing the remaining bases for incorporation (complementarity).

In FIG. 7, to sequence the next base on the template, the first identified base on the primer strand 710 is filled or replaced with an identified nuclease-resistant blocking nucleotide (3' blocking is indicated with a "'" in FIG. 7) that then becomes the priming base for the next test reaction after deblocking. In general, blocking nucleotides prevent further nucleic acid synthesis by reversibly blocking the addition of a nucleic acid to the end of the nucleic acid molecule. The blocking functionality of the nucleoside to be incorporated is optional. Nuclease-resistant blocking nucleosides are, for example, ribonucleosides or nucleosides modified, for example, at the 3' position with a azidomethyl, allyl, or O-nitrobenzyl group. A variety of polymerases are available that can incorporate ribonucleotides or modified nucleosides into DNA, such as for example, the commercially available Therminator DNA polymerase (available from New England Biolabs, Inc., Ipswitch, Mass.). See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant bases include alpha-phosphorothioate nucleosides having different chiralities, and exemplary nucleases that cannot digest the specific chiral isomer of the phosphorothioate bond include polymerase associated exonuclease such as the exonuclease activity of T4 or T7 Polymerase (which can not digest S-chiral conformation of the phosphorothioate bond). Some polymerase enzymes possess intrinsic exonuclease activity therefore it is not always necessary to use two different enzymes for the addition and excision reactions. Reactions in which no significant amount of product is detected indicate that the test reaction provided a nucleotide that was not complementary to the next base of the nucleic acid to be sequenced. After addition of the next known complementary nucleotide to the primer 710, the primer 710 is deblocked through removal of the 3' blocking group and the identity of the next complementary nucleotide is determined by repeating the test reactions as described above.

Reversible terminators that have been modified at the 3' position with, for example, 3'-azidomethyl or 3'-allyl, are cleaved chemically to deblock the nucleotide, using for example, TCEP (tricarboxylethylphosphine) for 3'-azidomethyl and aqueous Pd-based catalyst to remove 3'-allyl group, and 3'O-nitrobenzyl blocking groups are cleaved photochemically.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). The types of nucleic acids that are sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

Figure 8:
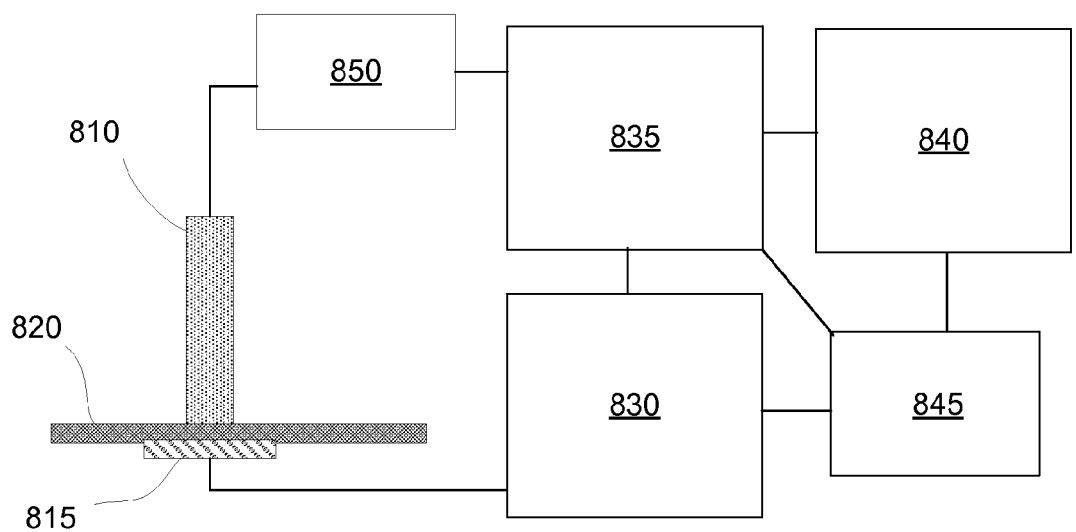
FIG. 8 diagrams a system for performing electronic detection using an array of sensors.

FIG. 8 diagrams a system useful for automating chemical and biochemical sensing using arrays of electronic sensors. The system of FIG. 8 is optionally fabricated as a portable device. In FIG. 8, an electronic fluidic interface 810 is fluidically coupled to an electronic sensor chip (not shown). The sensor chip is electrically attached to a socket (not shown) that provides electrical connections that are connected to external electronics. The socket is housed in the chip assembly substrate 815 that is optionally removably attached to an electronic fluidic interface substrate 820. The electronic fluidic interface substrate 820 also has the electronic fluidic interface 810 attached. The electronic fluidic interface 810 is fluidically sealed to the surface of the chip through a hole (not shown) in the electronic fluidic interface substrate 820. Other configurations for surrounding structure that holds the sensing chip and the electronic fluidic interface in a position so that a fluidic seal is formed between the sensing chip and the electronic fluidic interface are possible. The socket for the chip is electronically coupled to electronic circuitry 830 for driving the chip and measuring signals from the chip. Some of the electronic circuitry 830 is optionally contained in the chip itself. Optionally, the electronic circuitry 830 also provides thermal control for the chip. Also optionally, the sensor chip and socket or the sensor chip assembly 815 is a disposable unit that is removed once testing is finished and replaced with a new sensor device capable of analyzing additional or different molecules.

Optional thermal elements (not shown) are located within the chip assembly substrate 815, the socket, the chip, and or the electronic fluidic interface substrate 820. Exemplary methods of controlling the temperature of the sensor device include using thin metal films of Au, Ag, or Pt as resistive heaters and using a separate metal film (Pt or Au) as a temperature sensor to provide temperature feedback to the control circuitry 830. In additional embodiments, surrounding temperature control is provided. Surrounding temperature control consists of providing heating or cooling the sensor device through, for example, a thermal electric coupler (TEC) device (not shown) that is directly coupled to the chip assembly. Additionally optionally, devices are provided that are in communication with the chamber formed between the surface of the electronic sensing chip and the fluidic interface capable of measuring the pressure inside the chamber. Further optionally, control mechanisms for creating and or maintaining a selected pressure inside the chamber are provided. Electronic circuitry 830 couples the sensing chip to computing elements 835 running control software and provides for drive power inputs for the sensors, signal detection, and thermal control. Control software provides a user operation interface and controls temperature regulation functions, fluidic reagent delivery operations, and data collection, output, analysis, display, and or data storage operations. Some control software is optionally located in the chip itself. Computing elements 835 include software for displaying data related to the operation of the sensors and a display device. A storage device 840 stores for example software code, run routines, and or collected data. Electronic circuitry 830 also couples the optional reference electrode located in electronic fluidic interface 810 to the computing elements. A power source 845 (or one or more power sources) provides power to the system. Power sources include, for example, AC/DC converters and batteries.

Fluidic and reagent delivery systems 850 provide reagents to the fluidic interface 810. The fluidic delivery system 850 comprises tubing connecting the fluidic interface 810 to reservoirs holding reagents. Reagent delivery is automated through the computer software. Reagent delivery is mechanically accomplished using fluid delivery systems such as pumps, injectors, pressurized gases pushing the fluid, or vacuums pulling the fluid. Additionally, fluid delivery system optionally comprises a source of vacuum for removal of reagents from the sensing chip surface. Optionally, the system also includes a de-gassing system to remove gasses from fluids and prevent bubble formation, a mixer for reagent mixing, and a micro cooler for reagents to maintain reagent integrity.

In operation, to perform DNA sequencing reactions, such as, for example, those described in connection with FIG. 7 will require a plurality of solutions be delivered to the surface of the sensing chip for each sequencing run. For example, individual solutions each comprising one of the four nucleotides for nucleic acid synthesis and deconstruction are needed, as well as solutions comprising an enzyme solution containing DNA polymerase and exonuclease, and a second set of reservoirs containing modified nucleotides that are resistant to exonuclease. In some embodiments, the sensor is provided with reagents for sensing immobilized on or near the areas probed by the sensors. In other embodiments, the areas probed by the sensors are functionalized in situ with molecules to be analyzed or molecules that specifically bind molecules to be detected and or analyzed. Immobilizing DNA or other molecules on or near the areas probed by the sensors, includes the elements of cleaning the immobilization surface, introducing linking chemicals and attaching the DNA to be analyzed (or other molecule) on the surface. A wash fluid removes unwanted reagents and or products from the sensing regions before new solutions are introduced. Optionally, a special fluid such as an oil is used to encapsulate the whole assembly.

Advantageously, aspects of the present invention are embodied in a portable biosensing device. The electronic fluidic interface is also used for testing wafers. For testing wafers, a plurality of electronic fluidic interfaces is employed to test all or part of the sensor chips contained in the wafer or a raster is used to move the interface over the face of the wafer in order to test each chip in the wafer. Alternatively, a plurality of electronic and fluidic interfaces is moved over the surface of the wafer to test sensor chips.

Although exemplary uses for the electronic and fluidic interface are provided, the uses of the electronic and fluidic interface of the present invention are not limited to a particular type of electronic sensing.

Persons skilled in the relevant art appreciate that modifications and variations are possible throughout the disclosure and combinations and substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Furthermore, the particular features, structures, materials, or characteristics may be combined in any suitable manner in one or more embodiments. Various additional structures may be included and or described features may be omitted in other embodiments.

The invention claimed is:

1. A device comprising,
   a housing having an end, the end having a sealing member that is capable of forming a fluidic seal between the surface of an electronic sensor chip and the end of the housing,
   a plunger that fits inside the housing and that has one or more tubes located inside the plunger wherein the tubes are capable of delivering fluid from the outside of the housing to the surface of the electronic chip when the plunger is located inside the housing and the housing is associated with a sensor chip;
   wherein a chamber that is capable of retaining a liquid is formed proximal to a surface of the electronic sensor chip when the housing is associated with the electronic sensor chip and a fluidic seal is formed between the surface of the electronic sensor chip and the end of the housing, and
   a device substrate having a hole into which the end of the housing is capable of fitting and retaining member that retains the housing to the device substrate.

2. The device of claim 1 additionally including a retaining member attached to the housing to which a chip substrate comprising a sensor chip attached to a substrate is capable of attaching.

3. The device of claim 1 wherein a chip substrate comprising an electronic sensor chip attached to a substrate is capable of attaching to the device substrate.

4. The device of claim 1 wherein the plunger is removably attached inside the housing.

5. The device of claim 1 wherein the plunger assembly and the housing are one unit.

6. The device of claim 1 wherein the plunger comprises 2 to 25 tubes.

7. The device of claim 1 wherein the housing additionally comprises a hole through which a pressure can be maintained in the chamber that is formed proximal to the surface of the electronic sensor chip when the housing is associated with the electronic sensor chip.

8. The device of claim 1 additionally comprising an electronic sensor chip wherein the sealing member is positioned between a surface of the electronic sensor chip and the end of the housing so that a fluidic seal between the surface of the electronic sensor chip and the end of the housing is formed.

9. The device of claim 8 wherein the electronic sensor chip comprises an array of sensors and the sensors are selected from the group consisting of field effect transistors, extended gate field effect transistors, electrodes, and photon detectors.

10. The device of claim 1 wherein the plunger additionally comprises an electrode positioned so that it is capable of making contact with a liquid located in the chamber that is formed proximal to a surface of the electronic sensor chip when the housing is associated with the sensor chip.

11. The device of claim 1 wherein the plunger additionally comprises fiber optics capable of delivering light to the chamber that is formed proximal to a surface of the electronic sensor chip when the housing is associated with the sensor chip.

12. The device of claim 1 additionally comprising a fluid delivery system capable of delivering fluids to the tubes of the plunger, electronics capable of driving the sensor chip and collecting data from the sensor chip, a computer capable of interfacing with the electronics to drive the sensor chip and collect and analyze data from the sensor chip, and also capable of directing the operation of the fluid delivery system, and a memory capable of storing data from the sensor chip.

13. The device of claim 1 additionally comprising a source of reduced pressure capable of removing fluids from one or more tube(s) of the plunger.

14. A device comprising,
a housing having an end, the end being capable of attaching to a sealing member that is associated with the surface of an electronic sensor chip so that a fluidic seal is formed between the surface of an electronic sensor chip and the end of the housing, and
a plunger that fits inside the housing and that has one or more tubes located inside the plunger wherein the tubes are capable of delivering fluid from the outside of the housing to the surface of the electronic chip when the plunger is located inside the housing and the housing is associated with a sensor chip,
wherein a chamber that is capable of retaining a liquid is formed proximal to a surface of the electronic sensor chip when the housing is associated with the electronic sensor chip and a fluidic seal is formed between the surface of the electronic sensor chip and the end of the housing,
a device substrate having a hole into which the end of the housing is capable of fitting and retaining member that retains the housing to the device substrate.

15. The device of claim 14 additionally including a retaining member attached to the housing and to which a chip substrate comprising a sensor chip can be attached.

16. The device of claim 14 wherein a chip substrate comprising an electronic sensor chip is capable of attaching to the device substrate.

17. The device of claim 14 wherein the plunger is removably attached inside the housing.

18. The device of claim 14 wherein the plunger assembly and the housing are one unit.

19. The device of claim 14 wherein the plunge comprises 2 to 25 tubes.

20. The device of claim 14 additionally comprising an electronic sensor chip and a sealing member wherein the sealing member is positioned between a surface of the electronic sensor chip and the end of the housing so that a fluidic seal between the surface of the electronic sensor chip and the end of the housing is formed.

21. The device of claim 20 wherein the electronic sensor chip comprises an array of sensors and the sensors are selected from the group consisting of field effect transistors, extended gate field effect transistors, electrodes, and photon detectors.

22. The device of claim 14 wherein the plunger additionally comprises an electrode positioned so that it makes contact with a liquid retained in the chamber that is formed above an electronic sensor chip when the housing is associated with the sensor chip.

23. The device of claim 14 additionally comprising a fluid delivery system capable of delivering fluids to the tubes of the plunger, electronics capable of driving the electronic sensor chip and collecting data from the electronic sensor chip, a computer capable of interfacing with the electronics to drive the sensor chip and collect and analyze data from the electronic sensor chip, and also capable of directing the operation of the fluid delivery system, and a memory capable of storing data from the sensor chip.

24. The device of claim 14 additionally comprising a source of reduced pressure capable of removing fluids from one or more tube(s) of the plunger.

25. The device of claim 14 wherein the housing additionally comprises a hole through which a pressure can be maintained in the chamber that is formed proximal to the surface of the electronic sensor chip when the housing is associated with the electronic sensor chip.

* * * * *